(12) United States Patent
McAdon et al.

(10) Patent No.: US 6,268,445 B1
(45) Date of Patent: Jul. 31, 2001

(54) CATALYST ACTIVATOR

(75) Inventors: Mark H. McAdon; Peter N. Nickias, both of Midland, MI (US); Tobin J. Marks, Evanston, IL (US); David J. Schwartz, Lake Jackson, TX (US)

(73) Assignees: The Dow Chemical Company, Midland, MI (US); Northwestern University, Evanston, IL (US)

( * ) Notice: Subject to any disclaimer, the term of this patent is extended or adjusted under 35 U.S.C. 154(b) by 0 days.

(21) Appl. No.: 09/424,277

(22) PCT Filed: Jul. 7, 1998

(86) PCT No.: PCT/US98/14106
§ 371 Date: Nov. 19, 1999
§ 102(e) Date: Nov. 19, 1999

(87) PCT Pub. No.: WO99/06413
PCT Pub. Date: Feb. 11, 1999

Related U.S. Application Data
(60) Provisional application No. 60/054,586, filed on Aug. 1, 1997.

(51) Int. Cl.$^7$ .......................................................... C08F 4/52
(52) U.S. Cl. ........................... 526/134; 526/160; 526/943; 502/103; 502/152; 568/943
(58) Field of Search ...................................... 502/103, 152; 526/134, 160; 568/943, 3

(56) References Cited

U.S. PATENT DOCUMENTS 6,124,231 * 9/2000 Fritze et al. ........................ 502/152

* cited by examiner

*Primary Examiner*—David W. Wu
*Assistant Examiner*—Caixia Lu

(57) ABSTRACT

A catalyst activator particularly adapted for use in the activation of metal complexes of metals of Group 3–10 for polymerization of ethylenically unsaturated polymerizable monomers, especially olefins, comprising two Group 13 metal or metalloid atoms and a ligand structure including at least one bridging group connecting ligands on the two Group 13 metal or metalloid atoms.

15 Claims, No Drawings

CATALYST ACTIVATOR

CROSS REFERENCE TO RELATED APPLICATION

This application claims benefit of priority under 35 U.S.C. §371 of PCT/US98/14106, filed Jul. 7, 1998, which published under PCT Article 21(2) in the English language and which claims benefit of priority of provisional application No. 60/054,586, filed Aug. 1, 1997.

STATEMENT OF GOVERNMENTAL RIGHTS

The United States of America through the Department of Energy, is licensed to practice under the claims of this patent by means of DOE Grant No. DE-FG02-86ER13511.

The present invention relates to compounds that are useful as catalyst components. More particularly the present invention relates to such compounds that are particularly adapted for use in the coordination polymerization of unsaturated compounds comprising two Group 13 metal or metalloid atoms and a ligand structure including at least one bridging group connecting ligands on two Group 13 metal or metalloid atoms thereof. Such compounds are particularly advantageous for use in a polymerization process wherein catalyst, catalyst activator, and at least one polymerizable monomer are combined under polymerization conditions to form a polymeric product.

It is previously known in the art to activate Ziegler-Natta polymerization catalysts, particularly such catalysts comprising Group 3–10 metal complexes containing delocalized π-bonded ligand groups, by the use of Bronsted acid salts capable of transferring a proton to form a cationic derivative or other catalytically active derivative of such Group 3–10 metal complex. Preferred Bronsted acid salts are such compounds containing a cation/anion pair that are capable of rendering the Group 3–10 metal complex catalytically active. Suitable activators comprise fluorinated arylborate anions, most preferably, the tetrakis(pentafluorophenyl)borate anion. Additional suitable anions include sterically shielded diboron anions of the formula:

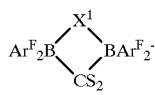

wherein:
S is hydrogen, alkyl, fluoroalkyl, aryl, or fluoroaryl, $Ar^F$ is fluoroaryl, and $X^1$ is either hydrogen or halide, disclosed in U.S. Pat. No. 5,447,895. Additional examples include carborane compounds such as are disclosed and claimed in U.S. Pat. No. 5,407,884.

Additional bisborane compounds lacking in aromatic bridging groups have been previously disclosed in U.S. Pat. No. 5,496,960, *Angew. Chem. Int. Ed. Engl.*, (1995) 34(7), 809–11, *Polyhedron*, (1997), 17(1), 119–124, *Organometallics*, (1994), 13(10) 3755–7, *Aust. J. Chem.* (1979), 32(11), 2381–93 and *Spectrochim, ACTA, PART A*, (1968), 24(8), 1125–33.

Examples of preferred charge separated (cation/anion pair) activators are protonated ammonium, sulfonium, or phosphonium salts capable of transferring a hydrogen ion, disclosed in U.S. Pat. No. 5,198,401, U.S. Pat. No. 5,132,380, U.S. Pat. No. 5,470,927, and U.S. Pat. No. 5,153,157, as well as oxidizing salts such as carbonium, ferrocenium and silyilium salts, disclosed in U.S. Pat. No. 5,350,723, U.S. Pat. No. 5,189,192 and U.S. Pat. No. 5,626,087.

Further suitable activators for the above metal complexes include strong Lewis acids including (trisperfluorophenyl)borane and tris(perfluorobiphenyl)borane. The former composition has been previously disclosed for the above stated end use in EP-A-520,732, whereas the latter composition is similarly disclosed by Marks, et al., in *J. Am. Chem. Soc.*, 118, 12451–12452 (1996).

Despite the satisfactory performance of the foregoing catalyst activators under a variety of polymerization conditions, there is still a need for improved cocatalysts for use in the activation of various metal complexes under a variety of reaction conditions. Accordingly, it would be desirable if there were provided compounds that could be employed in solution, slurry, gas phase or high pressure polymerizations and under homogeneous or heterogeneous process conditions having improved activation properties.

According to the present invention there is now provided Group 13 containing compounds useful as catalyst activators in neutral (Lewis acid) or charge separated (cation/anion pair) form, corresponding to the formula:

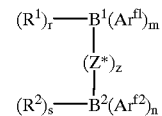

wherein:
$B^1$ and $B^2$ independently each occurrence are Group 13 metal or metalloid atoms, preferably boron;
$Z^*$ is an optional divalent bridging group containing from 1 to 20 atoms, not counting hydrogen atoms;
$R^1$ and $R^2$ independently each occurrence are monovalent, anionic ligand groups containing from 1 to 40 atoms not counting hydrogen atoms, and, for cationic compounds, additionally comprising a dissociated cation moiety;
$Ar^{f1}$ and $Ar^{f2}$ independently each occurrence are monovalent, fluorinated organic groups containing from 6 to 100 carbon atoms, optionally, an $Ar^{f1}$ and an $R^2$ group, or an $Ar^{f2}$ and an $R^1$ group together form a divalent bridging group, and further optionally an $Ar^{f1}$ group and an $Ar^{f2}$ group together form a $C_{6-100}$ divalent bridging group,
z is 0 or 1,
r and s independently are 0, 1 or 2, and
m and n are 1, 2 or 3;
with the proviso that when z is 0, at least one of $Ar^{f1}$ and $Ar^{f2}$ are joined together, and the sum of r, z and m is 3 or 4, in the former event $B^1$ is neutral and in the latter event $B^1$ is negatively charged, said charge being balanced by a cation component of one $R^1$; and the sum of s, z and n is 3 or 4, in the former event $B^2$ is neutral and in the latter event $B^2$ is negatively charged, said charge being balanced by a cation component of one $R^2$.

Additionally according to the present invention there is provided a catalyst composition for polymerization of an ethylenically unsaturated, polymerizable monomer comprising, in combination, the above described compound and a Group 3–10 metal complex, or the reaction product of such combination.

Additionally according to the present invention there is provided a process for polymerization of one or more ethylenically unsaturated, polymerizable monomers comprising contacting the same, optionally in the presence of an inert aliphatic, alicyclic or aromatic hydrocarbon, with the above catalyst composition.

The foregoing compounds are uniquely adapted for use in activation of a variety of metal complexes, especially Group 4 metal complexes, under standard and atypical olefin polymerization conditions. They are uniquely capable of forming monomeric and dimeric cationic metal complexes when combined with neutral metallocene complexes under such polymerization conditions. Because of this fact, the foregoing compounds are capable of forming highly desirable olefin polymers having enhanced levels of long chain branching, stereospecificity and comonomer distribution. In particular, bis-anions, due to the pairing of active catalyst sites in close proximity to one another, are capable of providing a higher local concentration of active catalyst site at the point of polymer formation. Moreover, such paired catalyst sites may be comprised of two disparate metals or metal ligand arrangements, or otherwise tailored to provide desirable polymer properties. For example, the use of symmetrical or unsymmetrical bis-anions results in two catalytically active sites that are held in close proximity during a polymerization reaction, thereby providing a large increase in local concentration of active catalyst sites. This increased local concentration of active catalyst sites leads to enhanced polymer stereostructure, molecular weight and microstructure. Certain catalyst sites in close proximity result in random comonomer incorporation, others affect the stereospecificity of their close neighbor. By controlling the random versus clustered distribution of comonomer, blocky or non-blocky copolymers can be prepared. Additionally, the two catalysts associated with each bis-anion may themselves be nonspecific or stereospecific, such that the resulting combination catalyst is adapted to produce block copolymers via polymer interchange between such nonspecific and stereospecific catalysts. The degree of long-chain branching in polyolefins produced using multiple catalyst sites on bis-anions is enhanced due to the rate of reincorporation of in situ generated vinyl terminated macromonomer into the growing polymer chain due to the higher local concentration of catalyst.

DETAILED DESCRIPTION OF THE INVENTION

All references herein to elements belonging to a certain Group refer to the Periodic Table of the Elements published and copyrighted by CRC Press, Inc., 1995. Also any reference to the Group or Groups shall be to the Group or Groups as reflected in this Periodic Table of the Elements using the IUPAC system for numbering groups. When, in reference to a cation portion of any compound herein, it is stated that a ligand group comprises such cation, it is to be understood that the cation is not chemically or physically incorporated in said ligand, or necessarily chemically attached thereto, in as much as the cation may freely dissociate from the anion portion of the compound. Rather, such ligand group is said to "comprise" the cation in order to properly account for the correct number of cations as dictated by considerations of charge balance.

The catalyst activators of the invention are further characterized in the following manner. Preferred Group 13 metal or metalloids include aluminum and boron. Most highly preferably, both $B^1$ and $B^2$ are boron. The cocatalysts may be neutral Lewis acids or salts comprising one or more cation-anion pairs. Examples of suitable neutral Lewis acids according to the present invention correspond to the formula:

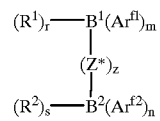

wherein all variables are as previously defined, and the sum of r, z and m and the sum of s, z and n are both 3.

More specific examples of the foregoing Lewis acid compounds correspond to the formula:

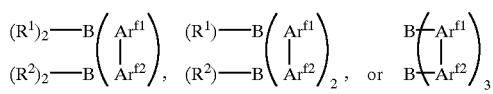

wherein:
  $R^1$ and $R^2$ independently each occurrence are $C_{1-20}$ hydrocarbyl, halohydrocarbyl, or halocarbyl, and
  $Ar^{f1}$–$Ar^{f2}$ in combination, independently each occurrence, is a divalent fluoro-substituted aromatic group of from 6 to 20 carbons.

Preferred examples of the foregoing Lewis acid compounds are the following:

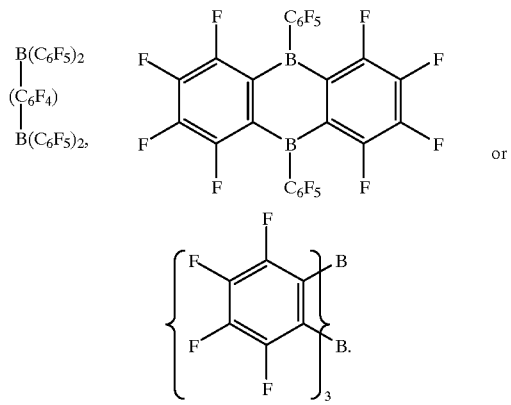

Examples of suitable charge separated compounds according to the present invention correspond to the formula:

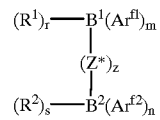

wherein:
  $R^1$ and $R^2$ independently each occurrence are $C_{1-20}$ hydrocarbyl, halohydrocarbyl, or halocarbyl groups, and (when the sum of r, z and m is 4) one $R^1$ additionally comprises a cation selected from the group consisting of protonated cations of Bronsted acids, ferrocenium cations, carbonium cations, silylium cations, and $Ag^+$, and (when the sum of s, z and n is 4) one $R^2$ additionally comprises a cation selected from the group consisting of protonated cations of Bronsted acids, ferrocenium cations, carbonium cations, silylium cations, and $Ag^+$;
  r and s are 0, 1 or 2 with the proviso that at least one of r or s is not 0, and the sum of r, z and m is 3 or 4 and the sum of s, z and n is 3 or 4, with the proviso that at least one of the foregoing sums is 4.

More specific examples of the foregoing charge separated compounds correspond to the formula:

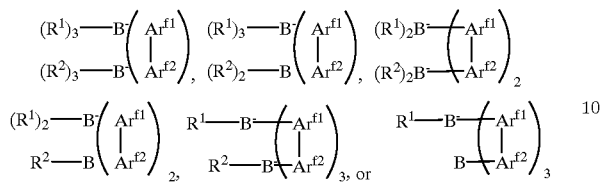

wherein:

$R^1$ and $R^2$ independently each occurrence are $C_{1-20}$ hydrocarbyl, halohydrocarbyl, or halocarbyl groups, and (when connected to a negatively charged boron atom) one $R^1$ additionally comprises a cation selected from the group consisting of protonated cations of Bronsted acids, ferrocenium cations, carbonium cations, silylium cations, and $Ag^+$, and (when connected to a negatively charged boron atom) one $R^2$ additionally comprises a cation selected from the group consisting of protonated cations of Bronsted acids, ferrocenium, carbonium cations, silylium cations, and $Ag^+$; and an $Ar^{f1}$ group and an $Ar^{f2}$ group together form a $C_{6-20}$ divalent fluoro-substituted aromatic group of from 6 to 20 carbons.

Specific examples of the foregoing salt compounds are the following:

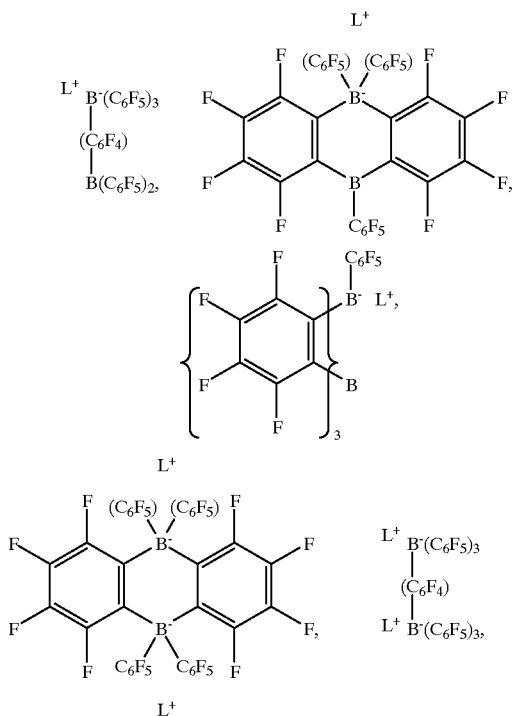

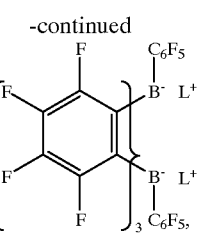

wherein, R is a $C_{1-40}$ hydrocarbyl ligand group, and $L^+$ is a cation of a Bronsted acid, or a ferrocenium, carbonium, silylium, or $Ag^+$ cation.

More preferably $L^+$ is an ammonium cation of the formula $HN^+R_3$, wherein R is $C_{1-50}$ hydrocarbyl. Most preferably, one or two R groups are $C_{14-50}$ aliphatic groups, and the remaining R group(s) is (are) $C_{1-4}$ aliphatic.

The skilled artisan will appreciate that upon activation of a metal complex to a catalytically active state by the present compounds, to the extent a cationic derivative thereof is formed, the foregoing charge separated compounds may include therein the cationic derivative of such metal complex in place of the foregoing Bronsted acid, ferrocenium, carbonium, silylium, or $Ag^+$ cations. For the preferred complexes the metal is selected from Groups 3–10 of the Periodic Table of the Elements, more preferably Group 4. Accordingly, such cationic derivative would be a Group 3–10 metal containing cation, more preferably a Group 4 metal containing cation.

Generally, solubility of the compounds of the invention in aliphatic compounds is increased by incorporation of one or more oleophilic groups such as long chain alkyl groups; long chain alkenyl groups; or halo-, alkoxy-, amino-, silyl-, or germyl-substituted long chain alkyl groups or long chain alkenyl groups into the cation, $L^+$. By the term "long chain" are meant groups having from 10 to 50 non-hydrogen atoms in such group, preferably in a non-branched form. It is understood that the compound may comprise a mixture of oleophilic groups of differing lengths in the cation. For example, one suitable compound comprises the protonated ammonium salt derived from the commercially available long chain amine comprising a mixture of two $C_{14}$, $C_{16}$ or $C_{18}$ alkyl groups and one methyl group. Such amines are available from Witco Corp., under the trade name Kemamine™ T9701, and from Akzo-Nobel under the trade name Armeen™ M2HT.

Suitable catalysts for use in combination with the foregoing cocatalysts include any compound or complex of a metal of Groups 3–10 of the Periodic Table of the Elements capable of being activated to polymerize ethylenically unsaturated compounds by the present activators. Examples include Group 10 diimine derivatives corresponding to the formula:

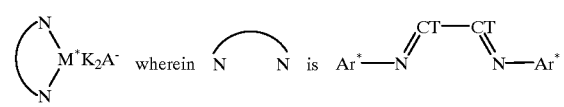

M* is Ni(II) or Pd(II);

K is halo, hydrocarbyl, or hydrocarbyloxy;

Ar* is an aryl group, especially 2,6-diisopropylphenyl or aniline group;

CT—CT is 1,2-ethanediyl, 2,3-butanediyl, or form a fused ring system wherein the two T groups together are a 1,8-naphthanediyl group; and A⁻ is the anionic component of the foregoing charge separated activators.

Similar catalysts to the foregoing are also disclosed by M. Brookhart, et al., in *J. Am. Chem. Soc.*, 118, 267–268(1996) and *J. Am. Chem. Soc.*, 117, 6414–6415 (1995), as being active polymerization catalysts especially for polymerization of α-olefins, either alone or in combination with polar comomoners such as vinyl chloride, alkyl acrylates and alkyl methacrylates.

Additional catalysts include derivatives of Group 3, 4, or Lanthanide metals which are in the +2, +3, or +4 formal oxidation state. Preferred compounds include metal complexes containing from 1 to 3 π-bonded anionic or neutral ligand groups, which may be cyclic or non-cyclic delocalized π-bonded anionic ligand groups. Exemplary of such π-bonded anionic ligand groups are conjugated or nonconjugated, cyclic or non-cyclic dienyl groups, allyl groups, boratabenzene groups, and arene groups. By the term "π-bonded" is meant that the ligand group is bonded to the transition metal by a sharing of electrons from a partially delocalized π-bond.

Each atom in the delocalized π-bonded group may independently be substituted with a radical selected from the group consisting of hydrogen, halogen, hydrocarbyl, halohydrocarbyl, hydrocarbyl-substituted metalloid radicals wherein the metalloid is selected from Group 14 of the Periodic Table of the Elements, and such hydrocarbyl- or hydrocarbyl-substituted metalloid radicals further substituted with a Group 15 or 16 hetero atom containing moiety. Included within the term "hydrocarbyl" are $C_{1-20}$ straight, branched and cyclic alkyl radicals, $C_{6-20}$ aromatic radicals, $C_{7-20}$ alkyl-substituted aromatic radicals, and $C_{7-20}$ aryl-substituted alkyl radicals. In addition two or more such radicals may together form a fused ring system, including partially or fully hydrogenated fused ring systems, or they may form a metallocycle with the metal. Suitable hydrocarbyl-substituted organometalloid radicals include mono-, di- and tri-substituted organometalloid radicals of Group 14 elements wherein each of the hydrocarbyl groups contains from 1 to 20 carbon atoms. Examples of suitable hydrocarbyl-substituted organometalloid radicals include trimethylsilyl, triethylsilyl, ethyidimethylsilyl, methyidiethylsilyl, triphenylgermyl, and trimethylgermyl groups. Examples of Group 15 or 16 hetero atom containing moieties include amine, phosphine, ether or thioether moieties or divalent derivatives thereof, e. g. amide, phosphide, ether or thioether groups bonded to the transition metal or Lanthanide metal, and bonded to the hydrocarbyl group or to the hydrocarbyl-substituted metalloid containing group.

Examples of suitable anionic, delocalized π-bonded groups include cyclopentadienyl, indenyl, fluorenyl, tetrahydroindenyl, tetrahydrofluorenyl, octahydrofluorenyl, pentadienyl, cyclohexadienyl, dihydroanthracenyl, hexahydroanthracenyl, decahydroanthracenyl groups, and boratabenzene groups, as well as $C_{1-10}$ hydrocarbyl-substituted or $C_{1-10}$ hydrocarbyl-substituted silyl substituted derivatives thereof. Preferred anionic delocalized π-bonded groups are cyclopentadienyl, pentamethylcyclopentadienyl, tetramethylcyclopentadienyl, tetramethylsilylcyclopentadienyl, indenyl, 2,3dimethylindenyl, fluorenyl, 2-methylindenyl, 2-methyl-4-phenylindenyl, tetrahydrofluorenyl, octahydrofluorenyl, and tetrahydroindenyl.

The boratabenzenes are anionic ligands which are boron containing analogues to benzene. They are previously known in the art having been described by G. Herberich, et al., in *Organometallics*, 14,1, 471–480 (1995). Preferred boratabenzenes correspond to the formula:

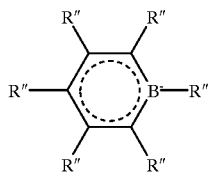

wherein R" is selected from the group consisting of hydrocarbyl, silyl, or germyl, said R" having up to 20 non-hydrogen atoms. In complexes involving divalent derivatives of such delocalized π-bonded groups one atom thereof is bonded by means of a covalent bond or a covalently bonded divalent group to another atom of the complex thereby forming a bridged system.

A suitable class of catalysts are transition metal complexes corresponding to the formula:

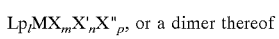

$Lp_lMX_mX'_nX''_p$, or a dimer thereof wherein:

Lp is an anionic, delocalized, π-bonded group that is bound to M, containing up to 50 non-hydrogen atoms, optionally two Lp groups may be joined together forming a bridged structure, and further optionally one Lp may be bound to X;

M is a metal of Group 4 of the Periodic Table of the Elements in the +2, +3 or +4 formal oxidation state;

X is an optional, divalent substituent of up to 50 non-hydrogen atoms that together with Lp forms a metallocycle with M;

X' is an optional neutral ligand having up to 20 non-hydrogen atoms;

X" each occurrence is a monovalent, anionic moiety having up to 40 non-hydrogen atoms, optionally, two X" groups may be covalently bound together forming a divalent dianionic moiety having both valences bound to M, or, optionally 2 X" groups may be covalently bound together to form a neutral, conjugated or nonconjugated diene that is π-bonded to M (whereupon M is in the +2 oxidation state), or further optionally one or more X" and one or more X' groups may be bonded together thereby forming a moiety that is both covalently bound to M and coordinated thereto by means of Lewis base functionality;

l is 0, 1 or 2;

m is 0 or 1;

n is a number from 0 to 3;

p is an integer from 0 to 3; and the sum, l+m+p, is equal to the formal oxidation state of M, except when 2 X" groups together form a neutral conjugated or non-conjugated diene that is π-bonded to M, in which case the sum l+m is equal to the formal oxidation state of M.

Preferred complexes include those containing either one or two Lp groups. The latter complexes include those containing a bridging group linking the two Lp groups. Preferred bridging groups are those corresponding to the formula $(ER^*_2)_x$ wherein E is silicon, germanium, tin, or carbon, R* independently each occurrence is hydrogen or a group selected from silyl, hydrocarbyl, hydrocarbyloxy and combinations thereof, said R* having up to 30 carbon or silicon atoms, and x is 1 to 8. Preferably, R* independently each occurrence is methyl, ethyl, propyl, benzyl, tert-butyl, phenyl, methoxy, ethoxy or phenoxy.

Examples of the complexes containing two Lp groups are compounds corresponding to the formula:

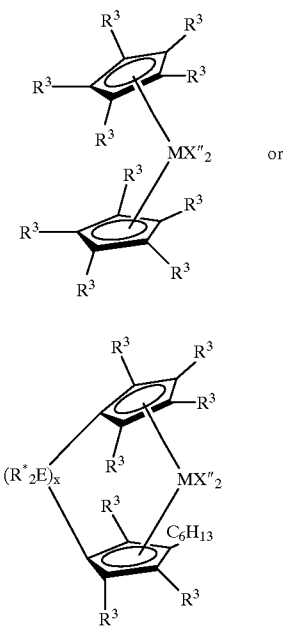

wherein:

M is titanium, zirconium or hafnium, preferably zirconium or hafnium, in the +2 or +4 formal oxidation state;

$R^3$ in each occurrence independently is selected from the group consisting of hydrogen, hydrocarbyl, silyl, germyl, cyano, halo and combinations thereof, said $R^3$ having up to 20 non-hydrogen atoms, or adjacent $R^3$ groups together form a divalent derivative (that is, a hydrocarbadiyl, siladiyl or germadiyl group) thereby forming a fused ring system, and X" independently each occurrence is an anionic ligand group of up to 40 non-hydrogen atoms, or two X" groups together form a divalent anionic ligand group of up to 40 non-hydrogen atoms or together are a conjugated diene having from 4 to 30 non-hydrogen atoms forming a π-complex with M, whereupon M is in the +2 formal oxidation state, and R*, E and x are as previously defined.

The foregoing metal complexes are especially suited for the preparation of polymers having stereoregular molecular structure. In such capacity it is preferred that the complex possesses $C_s$ symmetry or possesses a chiral, stereorigid structure. Examples of the first type are compounds possessing different delocalized π-bonded systems, such as one cyclopentadienyl group and one fluorenyl group. Similar systems based on Ti(IV) or Zr(IV) were disclosed for preparation of syndiotacfic olefin polymers in Ewen, et al., J. Am. Chem. Soc. 110, 6255–6256 (1980). Examples of chiral structures include rac bis-indenyl complexes. Similar systems based on Ti(IV) or Zr(IV) were disclosed for preparation of isotactic olefin polymers in Wild et al., J. Organomet. Chem., 232, 233–47, (1982).

Exemplary bridged ligands containing two π-bonded groups are: dimethylbis(cyclopentadienyl)silane, dimethylbis(tetramethylcyclopentadienyl)silane, dimethylbis(2-ethylcyclopentadien-1-yl)silane, dimethylbis(2-t-butylcyclopentadien-1-yl)silane, 2,2-bis (tetramethylcyclopentadienyl)propane, dimethylbis(inden-1-yl)silane, dimethylbis(tetrahydroinden-1-yl)silane, dimethylbis(fluoren-1-yl)silane, dimethylbis (tetrahydrofluoren-1-yl)silane, dimethylbis(2-methyl4-phenylinden-1-yl)-silane, dimethylbis(2-methylinden-1-yl) silane, dimethyl(cyclopentadienyl)(fluoren-1-yl)silane, dimethyl(cyclopentadienyl)(octahydrofluoren-1-yl)silane, dimethyl(cyclopentadienyl)(tetrahydrofluoren-1-yl)silane, (1,1,2,2-tetramethy)-1,2-bis(cyclopentadienyl)disilane, (1,2-bis(cyclopentadienyl)ethane, and dimethyl (cyclopentadienyl)-1-(fluoren-1-yl)methane.

Preferred X" groups are selected from hydride, hydrocarbyl, silyl, germyl, halohydrocarbyl, halosilyl, silylhydrocarbyl and aminohydrocarbyl groups, or two X" groups together form a divalent derivative of a conjugated diene or else together they form a neutral, π-bonded, conjugated diene. Most preferred X" groups are $C_{1-20}$ hydrocarbyl groups.

A further class of metal complexes utilized in the present invention corresponds to the preceding formula $Lp_lMX_mX'_nX''_p$, or a dimer thereof, wherein X is a divalent substituent of up to 50 non-hydrogen atoms that together with Lp forms a metallocycle with M.

Preferred divalent X substituents include groups containing up to 30 non-hydrogen atoms comprising at least one atom that is oxygen, sulfur, boron or a member of Group 14 of the Periodic Table of the Elements directly attached to the delocalized π-bonded group, and a different atom, selected from the group consisting of nitrogen, phosphorus, oxygen or sulfur that is covalently bonded to M.

A preferred class of such Group 4 metal coordination complexes used according to the present invention corresponds to the formula:

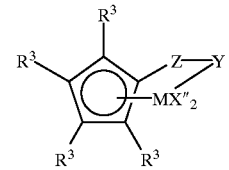

wherein:

M is titanium or zirconium, preferably titanium in the +2, +3, or +4 formal oxidation state;

$R^3$ in each occurrence independently is selected from the group consisting of hydrogen, hydrocarbyl, silyl, germyl, cyano, halo and combinations thereof, said $R^3$ having up to 20 non-hydrogen atoms, or adjacent $R^3$ groups together form a divalent derivative (that is, a hydrocarbadiyl, siladiyl or germadiyl group) thereby forming a fused ring system, each X" is a halo, hydrocarbyl, hydrocarbyloxy or silyl group, said group having up to 20 non-hydrogen atoms, or two X" groups together form a neutral $C_{5-30}$ conjugated diene or a divalent derivative thereof;

Y is —O—, —S—, —NR*—, —PR*—; and

Z is $SiR*_2$, $CR*_2$, $SiR*_2SiR*_2$, $CR*_2CR*_2$, $CR*=CR*$, $CR*_2SiR*_2$, or $GeR*_2$, wherein R* is as previously defined.

Illustrative Group 4 metal complexes that may be employed in the practice of the present invention include: cyclopentadienyltitaniumtrimethyl, cyclopentadienyltitaniumtriethyl, cyclopentadienyltitaniumtriisopropyl, cyclopentadienyltitaniumtriphenyl, cyclopentadienyltitaniumtribenzyl, cyclopentadienyltitanium-2,4-dimethylpentadienyl,
cyclopentadienyltitanium-2,4-dimethylpentadienyl•triethylphosphine,
cyclopentadienyltitanium-2,4-dimethylpentadienyl•trimethylphosphine,
cyclopentadienyltitaniumdimethylmethoxide,
cyclopentadienyltitaniumdimethylchloride,
pentamethylcyclopentadienyltitaniumtrimethyl,
indenyltitaniumtrimethyl,
indenyltitaniumtriethyl,
indenyltitaniumtripropyl,
indenyltitaniumtriphenyl,
tetrahydroindenyltitaniumtribenzyl,
pentamethylcyclopentadienyltitaniumtriisopropyl,
pentamethylcyclopentadienyltitaniumtribenzyl,
pentamethylcyclopentadienyltitaniumdimethylmethoxide,
pentamethylcyclopentadienyltitaniumdimethylchloride,
bis($\eta^5$-2,4-dimethylpentadienyl)titanium,
bis($\eta^5$-2,4-dimethylpentadienyl)titanium•trimethylphosphine,
bis($\eta^5$-2,4-dimethylpentadienyl)titanium•triethylphosphine,
octahydrofluorenyltitaniumtrimethyl,
tetrahydroindenyltitaniumtrimethyl,
tetrahydrofluorenyltitaniumtrimethyl,
(tert-butylamido)(1,1-dimethyl-2,3,4,9,10-$\eta$-1,4,5,6,7,8-hexahydronaphthalenyl)dimethylsilanetitaniumdimethyl,
(tert-butylamido)(1,1,2,3-tetramethyl-2,3,4,9,10-$\eta$-1,4,5,6,7,8-hexahydronaphthalenyl)dimethylsilanetitaniumdimethyl,
(tert-butylamido)(tetramethyl-$\eta^5$-cyclopentadienyl) dimethylsilanetitanium dibenzyl,
(tert-butylamido)(tetramethyl-$\eta^5$-cyclopentadienyl) dimethylsilanetitanium dimethyl,
(tert-butylamido)(tetramethyl-$\eta^5$-cyclopentadienyl)-1,2-ethanediyltitanium dimethyl,
(tert-butylamido)(tetramethyl-$\eta^5$-indenyl) dimethylsilanetitanium dimethyl,
(tert-butylamido)(tetramethyl-$\eta^5$-cyclopentadienyl) dimethylsilane titanium (III) 2-(dimethyiamino)benzyl;
(tert-butylamido)(tetramethyl-$\eta^5$-cyclopentadienyl) dimethylsilanetitanium (III) allyl,
(tert-butylamido)(tetramethyl-$\eta^5$-cyclopentadienyl) dimethylsilanetitanium (III) 2,4-dimethylpentadienyl,
(tert-butylamido)(tetramethyl-$\eta^5$-cyclopentadienyl) dimethylsilanetitanium (II) 1,4-diphenyl-1,3-butadiene,
(tert-butylamido)(tetramethyl-$\eta^5$-cyclopentadienyl) dimethylsilanetitanium (II) 1,3-pentadiene,
(tert-butylamido)(2-methylindenyl)dimethylsiianetitanium (II) 1,4diphenyl-1,3-butadiene,
(tert-butylamido)(2-methylindenyl)dimethylsilanetitanium (II) 2,4-hexadiene,
(tert-butylamido)(2-methylindenyl)dimethylsilanetitanium (IV) 2,3dimethyl-1,3-butadiene,
(tert-butylamido)(2-methylindenyl)dimethylsilanetitanium (IV) isoprene,
(tert-butylamido)(2-methylindenyl)dimethylsilanetitanium (IV) 1,3-butadiene,
(tert-butylamido)(2,3-dimethylindenyl) dimethylslianetitanium (IV) 2,3-dimethyl-1,3-butadiene,
(tert-butylamido)(2,3-dimethylindenyl) dimethylsilanetitanium (IV) isoprene
(tert-butylamido)(2,3-dimethylindenyl) dimethylsilanetitanium (IV) dimethyl
(tert-butylamido)(2,3-dimethylindenyl) dimethylsilanetitanium (IV) dibenzyl
(tert-butylamido)(2,3-dimethylindenyl) dimethylsilanetitanium (IV) 1,3-butadiene,
(tert-butylamido)(2,3-dimethylindenyl) dimethylsilanetitanium (II) 1,3-pentadiene,
(tert-butylamido)(2,3-dimethylindenyl) dimethylsilanetitanium (II) 1,4-diphenyl-1,3-butadiene,
(tert-butylamido)(2-methylindenyl)dimethylsilanetitanium (II) 1,3-pentadiene,
(tert-butylamido)(2-methylindenyl)dimethylsilanetitanium (IV) dimethyl,
(tert-butylamido)(2-methylindenyl)dimethylsilanetitanium (IV) dibenzyl,
(tert-butylamido)(2-methyl-4-phenylindenyl) dimethylsilanetitanium (II) 1,4-diphenyl-1,3-butadiene,
(tert-butylamido)(2-methyl-4-phenylindenyl) dimethylsilanetitanium (II) 1,3-pentadiene,
(tert-butylamido)(2-methyl-4-phenylindenyl) dimethylsilanetitanium (II) 2,4-hexadiene,
(tert-butylamido)(tetramethyl-$\eta^5$-cyclopentadienyl) dimethyl-silanetitanium (IV) 1,3-butadiene,
(tert-butylamido)(tetramethyl-$\eta^5$-cyclopentadienyl) dimethylsilanetitanium (IV) 2,3-dimethyl-1,3-butadiene,
(tert-butylamido)(tetramethyl-$\eta^5$-cyclopentadienyl) dimethylsilanetitanium (IV) isoprene,
(tert-butylamido)(tetramethyl-$\eta^5$-cyclopentadienyl) dimethyl-silanetitanium (II) 1,4-dibenzyl-1,3-butadiene,
(tert-butylamido)(tetramethyl-$\eta^5$-cyclopentadienyl) dimethylsilanetitanium (II) 2,4-hexadiene,
(tert-butylamido)(tetramethyl-$\eta^5$-cyclopentadienyl) dimethyl-silanetitanium (II) 3-methyl-1,3-pentadiene,
(tert-butylamido)(2,4-dimethylpentadien-3-yl) dimethylsilanetitaniumdimethyl,
(tert-butylamido)(6,6-dimethylcyclohexadienyl) dimethylsilanetitaniumdimethyl,
(tert-butylamido)(1,1-dimethyl-2,3,4,9,10-$\eta$-1,4,5,6,7,8-hexahydronaphthalen-4-yl) dimethylsilanetitaniumdimethyl,
(tert-butylamido)(1,1,2,3-tetramethyl-2,3,4,9,10-$\eta$-1,4,5,6,7,8-hexahydronaphthalen-4-yl) dimethylsilanetitaniumdimethyl
(tert-butylamido)(tetramethyl-$\eta^5$-cyclopentadienyl methylphenylsilanetitanium (IV) dimethyl,
(tert-butylamido)(tetramethyl-$\eta^5$-cyclopentadienyl methylphenylsilanetitanium (II) 1,4-diphenyl-1,3-butadiene,
1-(tert-butylamido)-2-(tetramethyl-$\eta^5$-cyclopentadienyi) ethanediyltitanium (IV) dimethyl, and
1-(tert-butylamido)-2-(tetramethyl-$\eta^5$-cyclopentadienyl) ethanediyltitanium (II) 1,4-diphenyl-1,3-butadiene.

Complexes containing two Lp groups including bridged complexes suitable for use in the present invention include:
bis(cyclopentadienyl)zirconiumdimethyl,
bis(cyclopentadienyl)zirconium dibenzyl,
bis(cyclopentadienyl)zirconium methyl benzyl,
bis(cyclopentadienyl)zirconium methyl phenyl,
bis(cyclopentadienyl)zirconiumdiphenyl,
bis(cyclopentadienyl)titanium-allyl,
bis(cyclopentadienyl)zirconiummethylmethoxide,
bis(cyclopentadienyl)zirconiummethylchloride,
bis(pentamethylcyclopentadienyl)zirconiumdimethyl,
bis(pentamethylcyclopentadienyl)titaniumdimethyl,
bis(indenyl)zirconiumdimethyl,
indenylfluorenylzirconiumdimethyl,
bis(indenyl)zirconiummethyl(2-(dimethylamino)benzyl),
bis(indenyl)zirconiummethyltrimethylsilyl,
bis(tetrahydroindenyl)zirconiummethyltrimethylsilyl,
bis(pentamethylcyclopentadienyl)zirconiummethylbenzyl,
bis(pentamethylcyclopentadienyl)zirconiumdibenzyl,
bis(pentamethylcyclopentadienyl) zirconiummethylmethoxide, bis(pentamethylcyclopentadienyl)zirconiummethylchloride,
bis(methylethylcyclopentadienyl)zirconiumdimethyl,
bis(butylcydopentadienyl)zirconiumdibenzyl,
bis(t-butylcyclopentadienyl)zirconiumdimethyl,
bis(ethyltetramethylcyclopentadienyl)zirconiumdimethyl,
bis(methylpropylcyclopentadienyl)zirconiumdibenzyl,
bis(trimethylsilylcyclopentadienyl)zirconiumdibenzyl,
dimethylsilyl-bis(cyclopentadienyl)zirconiumdimethyl,
dimethylsilyl-bis(tetramethylcyclopentadienyl)titanium (III) allyl
dimethylsilyl-bis(t-butylcyclopentadienyl) zirconiumdichloride,
dimethylsilyl-bis(n-butylcyclopentadienyl) zirconiumdichloride,
(methylene-bis(tetramethylcyclopentadienyl)titanium(III) 2-(dimethylamino)benzyl,
(methylene-bis(n-butylcyclopentadienyl)titanium(III) 2-(dimethylamino)benzyl,
dimethylsilyl-bis(indenyl)zirconiumbenzylchloride,
dimethylsilyl-bis(2-methylindenyl)zirconiumdimethyl,
dimethylsilyl-bis(2-methyl-4-phenylindenyl) zirconiumdimethyl,
dimethylsilyl-bis(2-methylindenyl)zirconium-1,4-diphenyl-1,3-butadiene,
dimethylsilyl-bis(2-methyl-4-phenylindenyl)zirconium (11) 1,4-diphenyl-1,3-butadiene,
dimethylsilyl-bis(tetrahydroindenyl)zirconium(II) 1,4-diphenyl-1,3-butadiene,
dimethylsilyl-bis(fluorenyl)zirconiummethylchloride,
dimethylsilyl-bis(tetrahydrofluorenyl)zirconium bis (trimethylsilyl),
(isopropylidene)(cyclopentadienyl)(fluorenyl) zirconiumdibenzyl, and
dimethylsilyl(tetramethylcyclopentadienyl)(fluorenyl) zirconium dimethyl.

Other catalysts, especially catalysts containing other Group 4 metals, will, of course, be apparent to those skilled in the art.

The cocatalysts of the invention may also be used in combination with a an oligomeric or polymeric alumoxane compound, a tri(hydrocarbyl)aluminum compound, a di(hydrocarbyl)(hydrocarbyloxy)aluminum compound, a di(hydrocarbyl)(dihydrocarbyl-amido)aluminum compound, a bis(dihydrocarbylamido)(hydrocarbyl) aluminum compound, a di(hydrocarbyl)amido(disilyl) aluminum compound, a di(hydrocarbyl)-amido (hydrocarbyl)(silyl)aluminum compound, a bis (dihydrocarbylamido)(silyl)aluminum compound, or a mixture of the foregoing compounds, having from 1 to 20 non-hydrogen atoms in each hydrocarbyl, hydrocarbyloxy, or silyl group, if desired. These aluminum compounds are usefully employed for their beneficial ability to scavenge impurities such as oxygen, water, and aldehydes from the polymerization mixture.

Preferred aluminum compounds include $C_{2-6}$ trialkyl aluminum compounds, especially those wherein the alkyl groups are ethyl, propyl, isopropyl, n-bulyl, isobutyl, pentyl, neopentyl, or isopentyl, dialkyl(aryloxy)aluminum compounds containing from 1–6 carbons in the alkyl group and from 6 to 18 carbons in the aryl group (especially (3,5-di (t-butyl)-4-methylphenoxy)diisobutylaluminum), methylalumoxane, modified methylalumoxane and diisobutylalumoxane. The molar ratio of aluminum compound to metal complex is preferably from 1:10,000 to 1000:1, more preferably from 1:5000 to 100:1, most preferably from 1:100 to 100:1.

The molar ratio of catalyst/cocatalyst employed preferably ranges from 10:1 to 1:10, more preferably from 2.1:1 to 1:1.5, most preferably from 2.05:1 to 1:1. Mixtures of the activating cocatalysts of the present invention may also be employed if desired.

Suitable addition polymerizable monomers include ethylenically unsaturated monomers, acetylenic compounds, conjugated or non-conjugated dienes, and polyenes. Preferred monomers include olefins, for examples alpha-olefins having from 2 to 20,000, preferably from 2 to 20, more preferably from 2 to 8 carbon atoms and combinations of two or more of such alphaolefins. Particularly suitable alpha-olefins include, for example, ethylene, propylene, 1-butene, 1-pentene, 4-methylpentene-1,1-hexene, 1-heptene, 1-octene, 1-nonene, 1-decene, 1-undecene, 1-dodecene, 1-tridecene, 1-tetradecene, 1-pentadecene, or combinations thereof, as well as long chain vinyl terminated oligomeric or polymeric reaction products formed during the polymerization, and $C_{1-30}$ α-olefins specifically added to the reaction mixture in order to produce relatively long chain branches in the resulting polymers. Preferably, the alpha-olefins are ethylene, propene, 1-butene, 4-methyl-pentene-1,1-hexene, 1-octene, and combinations of ethylene and/or propene with one or more of such other alpha-olefins. Other preferred monomers include styrene, halo- or alkyl substituted styrenes, tetrafluoroethylene, vinylcyclobutene, 1,4-hexadiene, dicyclopentadiene, ethylidene norbornene, and 1,7-octadiene. Mixtures of the above-mentioned monomers may also be employed.

In general, the polymerization may be accomplished at conditions well known in the prior art for Ziegler-Natta or Kaminsky-Sinn type polymerization reactions. Suspension, solution, slurry, gas phase or high pressure, whether employed in batch or continuous form or other process conditions, may be employed if desired. Examples of such well known polymerization processes are depicted in WO 88/02009, U.S. Pat. Nos. 5,084,534, 5,405,922, 4,588,790, 5,032,652, 4,543,399, 4,564,647, 4,522,987, and elsewhere. Preferred polymerization temperatures are from 0–250° C. Preferred polymerization pressures are from atmospheric to 3000 atmospheres.

Preferred processing conditions include solution polymerization, more preferably continuous solution polymerization processes, conducted in the presence of an aliphatic or alicyclic liquid diluent. By the term "continuous polymerization" is meant that at least the products of the polymerization are continuously removed from the reaction mixture, such as for example by devolatilization of a portion of the reaction mixture. Preferably one or more reactants are also continuously added to the polymerization mixture during the polymerization. Examples of suitable aliphatic or alicyclic liquid diluents include straight and branched-chain hydrocarbons such as isobutane, butane, pentane, hexane, heptane, octane, and mixtures thereof; alicyclic hydrocarbons such as cyclohexane, cydoheptane, methylcyclohexane, methylcycloheptane, and mixtures thereof; and perfluorinated hydrocarbons such as pertluorinated $C_{4-10}$ alkanes. Suitable diluents also include aromatic hydrocarbons (particularly for use with aromatic α-olefins such as styrene or ring alkyl-substituted styrenes) including toluene, ethylbenzene or xylene, as well as liquid olefins (which may act as monomers or comonomers) including ethylene, propylene, butadiene, cyclopentene, 1-hexene, 3-methyl-1-pentene, 4-methyl-1-pentene, 1,4-hexadiene, 1-octene, 1-decene, styrene, divinylbenzene, allylbenzene, vinyltoluene (including all isomers alone or in admixture). Mixtures of the foregoing are also suitable.

In most polymerization reactions the molar ratio of catalyst:polymerizable compounds employed is from $10^{-12}:1$ to $10^{-1}:1$, more preferably from $10^{-12}:1$ to $10^{-5}:1$.

The catalyst composition of the invention may also be utilized in combination with at least one additional homogeneous or heterogeneous polymerization catalyst in separate reactors connected in series or in parallel to prepare polymer blends having desirable properties. An example of such a process is disclosed in WO 94/00500, equivalent to U.S. Ser. No. 07/904,770 ABN. A more specific process is disclosed in copending application U.S. Ser. No. 08/10958, filed Jan. 29, 1993 ABN.

Molecular weight control agents can be used in combination with the present cocatalysts. Examples of such molecular weight control agents include hydrogen, trialkyl aluminum compounds or other known chain transfer agents. A particular benefit of the use of the present cocatalysts is the ability (depending on reaction conditions) to produce narrow molecular weight distribution α-olefin homopolymers and copolymers in greatly improved catalyst efficiencies. Preferred polymers have Mw/Mn of less than 2.5, more preferably less than 2.3. Such narrow molecular weight distribution polymer products are highly desirable due to improved tensile strength properties.

The catalyst composition of the present invention can also be employed to advantage in the gas phase polymerization and copolymerization of olefins. Gas phase processes for the polymerization of olefins, especially the homopolymerization and copolymerization of ethylene and propylene, and the copolymerization of ethylene with higher alpha olefins such as, for example, 1-butene, 1-hexene, 4-methyl-1-pentene are well known in the art. Such processes are used commercially on a large scale for the manufacture of high density polyethylene (HDPE), medium density polyethylene (MDPE), linear low density polyethylene (LLDPE) and polypropylene.

The gas phase process employed can be, for example, of the type which employs a mechanically stirred bed or a gas fluidized bed as the polymerization reaction zone. Preferred is the process wherein the polymerization reaction is carried out in a vertical cylindrical polymerization reactor containing a fluidized bed of polymer particles supported above a perforated plate, the fluidisation grid, by a flow of fluidisation gas.

The gas employed to fluidize the bed comprises the monomer or monomers to be polymerized, and also serves as a heat exchange medium to remove the heat of reaction from the bed. The hot gases emerge from the top of the reactor, normally via a tranquilization zone, also known as a velocity reduction zone, having a wider diameter than the fluidized bed and wherein fine particles entrained in the gas stream have an opportunity to gravitate back into the bed. It can also be advantageous to use a cyclone to remove ultra-fine particles from the hot gas stream. The gas is then normally recycled to the bed by means of a blower or compressor and a one or more heat exchangers to strip the gas of the heat of polymerization.

A preferred method of cooling of the bed, in addition to the cooling provided by the cooled recycle gas, is to feed a volatile liquid to the bed to provide an evaporative cooling effect. The volatile liquid employed in this case can be, for example, a volatile inert liquid, for example, a saturated hydrocarbon having 3 to 8, preferably 4 to 6, carbon atoms. In the case that the monomer or comonomer itself is a volatile liquid, or can be condensed to provide such a liquid this can be suitably be fed to the bed to provide an evaporative cooling effect. Examples of olefin monomers which can be employed in this manner are olefins containing from 3 to eight, preferably from 3 to six carbon atoms. The volatile liquid evaporates in the hot fluidized bed to form gas which mixes with the fluidizing gas. If the volatile liquid is a monomer or comonomer, it will undergo some polymerization in the bed. The evaporated liquid then emerges from the reactor as part of the hot recycle gas, and enters the compression/heat exchange part of the recycle loop. The recycle gas is cooled in the heat exchanger and, if the temperature to which the gas is cooled is below the dew point, liquid will precipitate from the gas. This liquid is desirably recycled continuously to the fluidized bed. It is possible to recycle the precipitated liquid to the bed as liquid droplets carried in the recycle gas stream, as described, for example, in EP-A-89691, U.S. Pat. No. 4,543,399, WO 94/25495 and U.S. Pat. No. 5,352,749. A particularly preferred method of recycling the liquid to the bed is to separate the liquid from the recycle gas stream and to reinject this liquid directly into the bed, preferably using a method which generates fine droplets of the liquid within the bed. This type of process is described in WO 94/28032.

The polymerization reaction occurring in the gas fluidized bed is catalyzed by the continuous or semi-continuous addition of catalyst. [Such catalyst can be supported on an inorganic or organic support material if desired. The catalyst can also be subjected to a prepolymerization step, for example, by polymerizing a small quantity of olefin monomer in a liquid inert diluent, to provide a catalyst composite comprising catalyst particles embedded in olefin polymer particles.

The polymer is produced directly in the fluidized bed by catalyzed (co)polymerization of the monomer(s) on the fluidized particles of catalyst, supported catalyst or prepolymer within the bed. Start-up of the polymerization reaction is achieved using a bed of preformed polymer particles, which, preferably, is similar to the target polyolefin, and conditioning the bed by drying with inert gas or nitrogen prior to introducing the catalyst, the monomer(s) and any other gases which it is desired to have in the recycle gas stream, such as a diluent gas, hydrogen chain transfer agent, or an inert condensable gas when operating in gas phase condensing mode. The produced polymer is discharged continuously or discontinuously from the fluidized bed as desired, optionally exposed to a catalyst kill and optionally pelletized.

It is understood that the present invention is operable in the absence of any component which has not been specifically disclosed. The following examples are provided in order to further illustrate the invention and are not to be construed as limiting. Unless stated to the contrary, all parts and percentages are expressed on a weight basis.

EXAMPLE 1

Preparation of (tetrafluoro-1,4-phenylene)-bis-(di (pentafluorophenyl)borane) (($C_6F_6)_2$ B—$C_6F_4$—B $(C_6F_5)_2$)

Into a thick-walled flask containing a J. Young valve, 1,4-$C_6F_4(SnMe_3)_2$ (0.60 g, 1.26 mmol) and $(C_6F_5)_2BCl$ (2.87 g, 7.56 mmol) were added. Toluene (40 mL) was added, the flask was evacuated to 0.1 torr, and the J. Young valve was closed. The flask was heated at 140° C. for 72 h. The solvent was removed in vacuo, and the residue washed with pentane (4×20 mL). The resulting light yellow solid was exposed to dynamic vacuum ($10^{-5}$ torr) for 12 h, giving the desired product as a microcrystalline pale yellow solid (0.75 g, 71 percent).

$^{19}$F NMR ($CD_2Cl_2$): δ −125.7 (br, 8F, ortho $C_6F_5$), −128.2 (br, 4F, $C_6F_4$), −141.1 (br, 4F, para $C_6F_5$), −159.1 (br, 8F, meta $C_6F_5$) ppm. MS (EI, 6.3 V): m/e 838 ($M^+$, 100 percent).

Activation of Metal Complex

Combination of the diborane compound of Example 1 with the zirconocene biscyclopentadienylzirconium dimethyl in $CD_2Cl_2$ at 25° C. in a 1:1 and a 2:1 atomic ratio (Zr:B) gave two cationic reaction products corresponding to the monoanionic salt (1) and the dianionic salt (2) derivatives according to the following scheme.

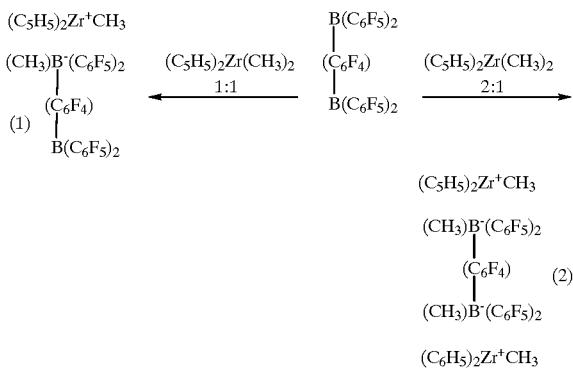

NMR data for 1: $^1H$ NMR ($CD_2Cl_2$): δ 6.39 (s, 10H), 0.68 (s, 3H), 0.31 (br, 3H) ppm. $^{19}F$ NMR ($CD_2Cl_2$): δ −127.5 (d, $^3J_{FF}$=21 Hz, 3F), −129.3 (t, $^3J_{FF}$=18 Hz, 1F), −131.8 (m, 1F), −132.4 (m, 6F), −136.7 (s, 1F:), −144.8 (s, 1F), −159.0 (br, 1F), −160.0 (m, 4F), −163.8 (br, 2F), −164.2 (t, $^3J_{FF}$=19 Hz, 3F).

NMR data for 2: $^1H$ NMR ($CD_2Cl_2$): δ 6.29 (s, 20H), 0.45 (br, 6H), 0.29 (br, 6H) ppm. $^{19}F$ NMR ($CD_2Cl_2$): δ −131.5 (d, $^3J_{FF}$=18 Hz, 8F, ortho $C_6F_5$), −142.8 (br, 4F, $C_6F_5$), −162.4 (br, 4F, para $C_6F_5$), −165.3 (br, 8F, meta $C_6F_5$) ppm.

EXAMPLE 2

Preparation of (tetrafluoro-1,2-phenylene)-bis-(di(pentafluorophenyl)borane)

A) Preparation of $[1,2-C_6F_4BCl]_2$

Excess $BCl_3$ (ca. 5.0 g, 44 mmol) was condensed into a thick-walled flask containing a J. Young valve and $1,2-C_6F_4(SnMe_3)_2$ (5.3 g, 11.1 mmol), at −196° C. The flask was evacuated to 0.05 torr, and the J. Young valve was closed. The reaction mixture was heated at 180° C. for 18 h. The excess $BCl_3$ was removed under dynamic vacuum, giving a slightly moist, beige solid. The product was extracted with pentane (3×20 mL), leaving behind 65 percent of the $Me_3SnCl$ byproduct. The remaining $Me_3SnCl$ was sublimed away at 40° C./$10^{-5}$ torr. The product was then sublimed at 90° C./$10^{-5}$ torr, giving $[1,2-C_6F_4BCl]_2$ as a yellow solid (1.15 g, 53 percent).

$^{19}F$ NMR ($C_6D_6$): δ −122.7 (m, 4F), −143.9 (m, 4F) ppm.
$^{13}C$ NMR ($CDCl_3$): δ 152.6 (d, $^1J_{CF}$=262 Hz), 144.6 (d, $^1J_{CF}$=260 Hz), 122.8 (br, B-C) ppm. MS (EI, 8.7 V) (percent intensity): 392 (16), 391 (18), 390 (67), 389 (M+, 47), 388 (100), 387 (51), 342 (21), 318 (22), 304 (28), 250 (25), 201 (30). Anal. Calcd for $C_{12}F_8B_2Cl_2$: C, 37.1; H, 0.0. Found: C, 38.2; H. 0.3.

B) Preparation of $[1,2-C_6F_4B(C_6F_5)]_2$,

Into a thick-walled flask containing a J. Young valve, $[1,2-C_6F_4BCl]_2$ (0.265 g, 0.68 mmol) and $(C_6F_5)_2SnMe_2$ (0.33 g, 0.68 mmol) were placed. Toluene (20 mL) was added, the flask was evacuated to 0.1 torr, and the J. Young valve was closed. The reaction solution was heated to 140° C. for 72 h, giving a bright yellow solution. The solution was concentrated to 10 mL, and then heated to dissolve all solids. Slow cooling of this solution to −78° C. gave 2 as light yellow crystals. This solid was found to contain a small amount of $Me_2SnCl_2$, which can be removed under dynamic vacuum ($10^{-5}$ torr/12 h), giving the desired product, $[1,2-C_6F_4B(C_6F_5)]_2$, as a light yellow crystalline solid (0.35 g, 68 percent). Alternatively, because of the sensitivity of the compound, the crude reaction solution can be exposed to dynamic vacuum ($10^{-5}$ torr) for 12 h, giving the product in >95 percent purity, without the need for crystallization.

$^{19}F$ NMR ($d_8$-toluene): δ −118.2 (br, 4F, ortho $C_6F_4$), −133.9 (dd, $^3J_{FF}$=25.1 Hz; $^4J_{FF}$=7.9 Hz, 4F, ortho $C_6F_5$), −138.9 (m, 4F, meta $C_6F_4$), −152.1 (t, $^3J_{FF}$=21 Hz, 2F, para $C_6F_5$), −161.4 (ddd, $^3J_{FF}$=22 Hz; $^3J_{FF}$=22 Hz, $^5J_{FF}$=7 Hz, 4F, meta $C_6F_5$) ppm.
$^{13}C$ NMR ($CDCl_3$): δ 156.1 (d, $^1J_{CF}$=267 Hz), 145.9 (d, $^1J_{CF}$=265 Hz), 144.3 (d, $^J_{CF}$=241 HZ), 141.6 (d, $^1J_{CF}$=265 Hz), 137.6 (d, $^1J_{CF}$=253 Hz), 128.3 (br), 23.7 (br) ppm.

Crystal Data $C_{24}F_{18}B_2$•$(2C_7H_8)$; monoclinic, space group $P2_1/c$; a =22.836(4), b=0.846(3), c=13.767(3) Å; b=99.66(2)°; V=3361 (1) Å$^3$; Z=4; $d_{calcd}$=1.652 g/cm$^3$; at −120° C. The structure was solved by direct methods. Owing to the paucity of data, the fluorine atoms were refined anisotropically and the remaining non-hydrogen atoms were refined isotropically. Hydrogen atoms were included in "idealized" positions and not refined. The final cycle of full-matrix least-squares refinement was based on 2042 observed reflections (I>3.00 σ(l)) and 324 variable parameters and converged (largest parameter shift was 0.12 times its esd) with unweighted and weighted agreement factors of R=0.051 and $R_w$=0.039. For clarity of the crystallographic discussion, it should be noted that there are two half molecules in the asymmetric unit, and consequently there are two independent bond distances and angles for each bond distancelangle of 2.

Activation of Metal Complexes

Combination of the diborane compound of Example 2 with the zirconocene biscyclopentadienylzirconium dimethyl in $CD_2Cl_2$ at 25° C. in a 1:1 and a 2:1 atomic ratio (Zr:B) gave two cationic reaction products corresponding to the monoanionic salt (3) and the dianionic salt (4) derivatives according to the following scheme.

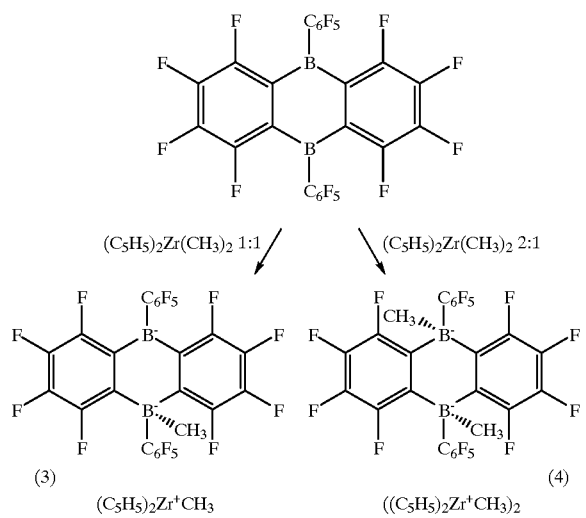

NMR data for 3: $^{19}F$ ($CD_2Cl_2$, 25° C.): δ −123.1 (br, 2F), −132.4 (m, 3F), −134.0 (br, 2F), −134.8 (br, 1F), −145.0 (br, 2F), −155.4 (t, $^3J_{FF}$=21 Hz, 1F), −158.9 (m, 2F), −160.0 (m, 1F), −161.8 (br, 1F), −162.5 (br, 1F), −164.1 (br, t, $^3J_{FF}$=21 Hz, 2F) ppm.

$^1$H (CD$_2$Cl$_2$, 25° C.): δ 6.34 (s, 10H), 0.66 (s, 3H), 0.17 (br, 3H) ppm.

NMR data for 4: $^{19}$F (CD$_2$Cl$_2$, 25° C.): δ −132.7 (br, 2F, ortho C$_6$F$_5$), −134.7 (br, 4F, ortho C$_6$F$_4$), −136.4 (br, 2F, ortho C$_6$F$_5$), −161.6 (t, $^3J_{FF}$=20 Hz, 2F, pare C$_6$F$_5$), −162.6 (d, $^3J_{FF}$=19 Hz, 4F, meta C$_6$F$_4$), −164.4 (br, 2F, meta C$_6$F$_5$), −165.4 (br, 2F, meta C$_6$F$_5$) ppm. $^1$H (CD$_2$Cl$_2$, 25° C.): 0 6.22 (s, 10H), 0.69 (s, 3H), 0.19 (br, 3H) ppm; a slight excess of (C$_5$H$_5$)$_2$ZrMe$_2$ was present in this sample, and resonances attributable to this compound are also present.

Polymerizations

A two liter stirred reactor was charged with 640 mL Isopar™ E solvent, and 150 g of propylene. Hydrogen (25 ml at 35 Δpsi, 0.2 ΔMPa) was added as a molecular weight control agent. The reactor was heated to 70° C. The catalyst composition was prepared in a drybox by mixing together 0.005M toluene solutions of (tbutylamido)dimethyl(η$^5$-tetramethylcyclopentadienyl)titanium dimethyl catalyst, and the compounds of examples 1 or 2 to give atomic ratios of B/Ti of 1:1 or 2:1. After a mixing time of 5 minutes the solutions were then transferred to an addition loop and injected into the reactor. The polymerization was allowed to proceed for 10 minutes while maintaining the reaction temperature at 70° C. The polymer solution was transferred from the reactor into a glass kettle and dried in a vacuum oven for 16 hours at a maximum temperature of 120° C. Results are contained in Table 1.

TABLE 1

| run | μmol catalyst | cocatalyst (μmol) | reaction time min. | g polymer | efficiency (Kg polymer/ g Ti) |
|---|---|---|---|---|---|
| 1* | 6 | FAB$^1$ (6) | 10 | 29.7 | 103 |
| 2 | 0.75 | Ex. 2 (0.75) | 10 | 70.9 | 1,974 |
| 3* | 6 | FAB$^1$ (6) | 10 | 37.0 | 129 |
| 4 | 1.5 | Ex. 2 (0.75) | 10 | 66.4 | 925 |
| 5 | 3 | Ex. 1 (3) | 18.5 | 29.7 | 207 |
| 6 | 6 | Ex. 1 (3) | 10 | 49.2 | 171 |

*not an example of the invention
$^1$tris(pentafluorophenyl)borane

What is claimed is:

1. A compound corresponding to the formula:

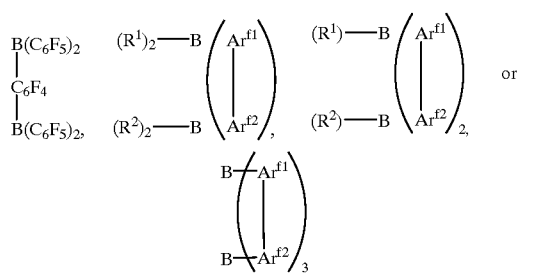

wherein:

R$^1$ and R$^2$ independently each occurrence are C$_{1-20}$ hydrocarbyl, halohydrocarbyl, or halocarbyl groups, and Ar$^{f1}$–Ar$^{f2}$ in combination, independently each occurrence, is a divalent fluoro-substituted aromatic group of from 6 to 20 carbons.

2. The compound of claim 1 corresponding to the formula:

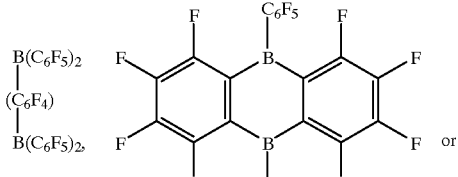

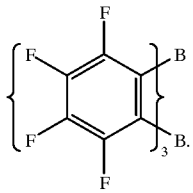

3. A compound corresponding to the formula:

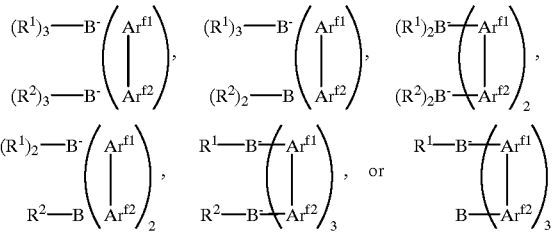

wherein:

R$^1$ and R$^2$ independently each occurrence are C$_{1-20}$ hydrocarbyl, halohydrocarbyl, or halocarbyl groups, and when connected to a negatively charged boron atom, one R$^1$ additionally comprises a cation selected from the group consisting of protonated cations of Bronsted acids, ferrocenium cations, carbonium cations, silylium cations, Ag$^+$, and cationic derivatives of a Group 3–10 metal complex and when connected to a negatively charged boron atom, one R$^2$ additionally comprises a cation selected from the group consisting of protonated cations of Bronsted acids, ferrocenium, carbonium cations, silylium cations, Ag$^+$, and cationic derivatives of a Group 3–10 metal complex; and an Ar$^{f1}$ group and an Ar$^{f2}$ group together form a C$_{6-20}$ divalent bridging group.

4. A compound according to claim 3 corresponding to the formula:

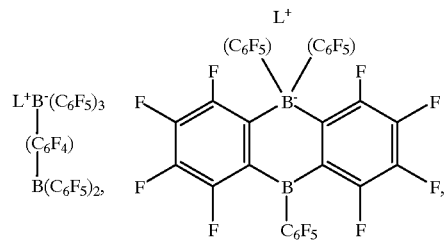

-continued

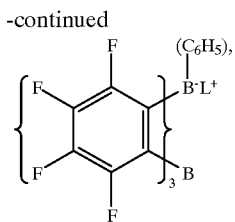

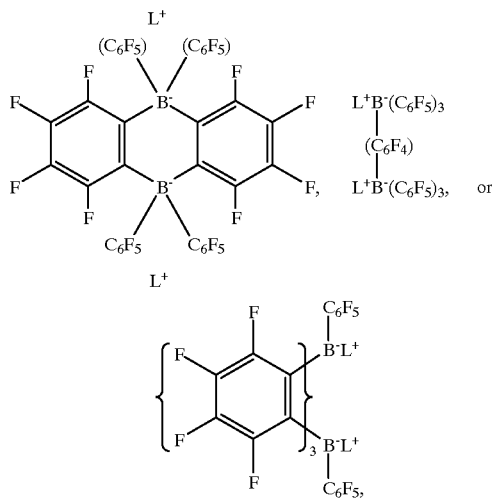

wherein, L⁺ is a cation of a Bronsted acid, or a ferrocenium, carbonium, silylium, or Ag⁺ cation.

5. A catalyst system for polymerization of α-olefins comprising, in combination, a Group 4 metal complex and a compound according to any one of claims 1–4, or the reaction product thereof.

6. A polymerization process comprising contacting one or more α-olefins under polymerization conditions with a catalyst system according to claim 5.

7. A process according to claim 6 which is a solution polymerization.

8. A polymerization process according to claim 7 that is a continuous solution polymerization.

9. A polymerization process according to claim 6 that is a gas phase polymerization.

10. The compound of claim 4 wherein L⁺ is HN⁺R₃ where R is $C_{1-50}$ hydrocarbyl.

11. The compound of claim 10 wherein one or two R groups are $C_{14-50}$ aliphatic groups and the remaining R groups or group is $C_{1-4}$ aliphatic.

12. The catalyst system of claim 5 wherein the Group 4 metal complex corresponds to the formula:

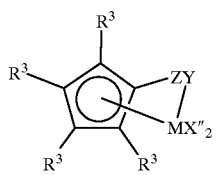

wherein:
M is titanium in the +4 formal oxidation state;
$R^3$ in each occurrence independently is selected from the group consisting of hydrogen, hydrocarbyl, silyl, germyl, cyano, halo and combinations thereof, said $R^3$ having up to 20 non-hydrogen atoms, or adjacent $R^3$ groups together form a divalent derivative thereby forming a fused ring system,
each X″ is a halo, hydrocarbyl, hydrocarbyloxy or silyl group, said group having up to 20 non-hydrogen atoms, or two X″ groups together form a divalent derivative of a $C_{5-30}$ conjugated diene;
Y is —O—, —S—, —NR*—, —PR*—; and
Z is SiR*₂, CR*₂, SiR*₂SiR*₂, CR*₂CR*₂, CR*=CR*, CR*₂SiR*₂, or GeR*₂, wherein R* is hydrogen or a group selected from silyl, hydrocarbyl, hydrocarbyloxy and combinations thereof, said R* having up to 30 carbon or silicon atoms.

13. A catalyst system for polymerization of α-olefins comprising, the combination or reaction product of a Group 4 metal complex corresponding to the formula:

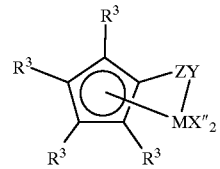

wherein:
M is titanium in the +4 formal oxidation state;
$R^3$ in each occurrence independently is selected from the group consisting of hydrogen, hydrocarbyl, silyl, germyl, cyano, halo and combinations thereof, said $R^3$ having up to 20 non-hydrogen atoms, or adjacent $R^3$ groups together form a divalent derivative thereby forming a fused ring system,
each X″ is a halo, hydrocarbyl, hydrocarbyloxy or silyl group, said group having up to 20 non-hydrogen atoms, or two X″ groups together form a divalent derivative of a $C_{5-30}$ conjugated diene;
Y is —O—, —S—, —NR*—, —PR*—; and
Z is SiR*₂, CR*₂, SiR*₂SiR*₂, CR*₂CR*₂, CR*=CR*, CR*₂SiR*₂, or GeR*₂, wherein R* is hydrogen or a group selected from silyl, hydrocarbyl, hydrocarbyloxy and combinations thereof, said R* having up to 30 carbon or silicon atoms, and
a compound corresponding to the formula:

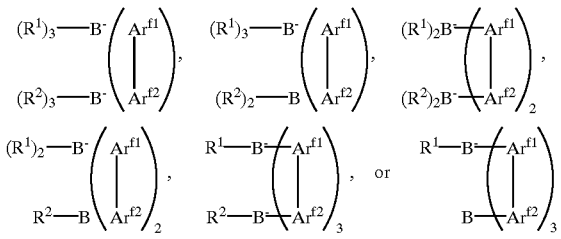

wherein:
$R^1$ and $R^2$ independently each occurrence are $C_{1-20}$ hydrocarbyl, halohydrocarbyl, or halocarbyl groups, and when connected to a negatively charged boron atom, one $R^1$ additionally comprises a cation selected from the group consisting of protonated cations of Bronsted acids, ferrocenium cations, carbonium cations, silylium cations, Ag⁺, and cationic derivatives of a Group 3–10 metal complex and when connected to a negatively charged boron atom, one $R^2$ additionally comprises a cation selected from the group consisting of protonated cations of Bronsted acids, ferrocenium, carbonium cations, silylium cations, $Ag^+$, and cationic derivatives of a Group 3–10 metal complex; and an $Ar^{f1}$ group and an $Ar^{f2}$ group together form a $C_{6-20}$ divalent bridging group.

14. A catalyst system for polymerization of α-olefins comprising, the combination or reaction product of a Group 4 metal complex corresponding to the formula:

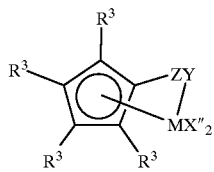

wherein:
M is titanium in the +2 formal oxidation state;
$R^3$ in each occurrence independently is selected from the group consisting of hydrogen, hydrocarbyl, silyl, germyl, cyano, halo and combinations thereof, said $R^3$ having up to 20 non-hydrogen atoms, or adjacent $R^3$ groups together form a divalent derivative thereby forming a fused ring system, two X" groups together form a neutral $C_{5-30}$ conjugated diene;

Y is —O—, —S—, —NR*—, —PR*—; and

Z is $SiR^*_2$, $CR^*_2$, $SiR^*_2SiR^*_2$, $CR^*_2CR^*_2$, $CR^*=CR^*$, $CR^*_2SiR^*_2$, or $GeR^*_2$, wherein $R^*$ is hydrogen or a group selected from silyl, hydrocarbyl, hydrocarbyloxy and combinations thereof, said $R^*$ having up to 30 carbon or silicon atoms, and a compound corresponding to the formula:

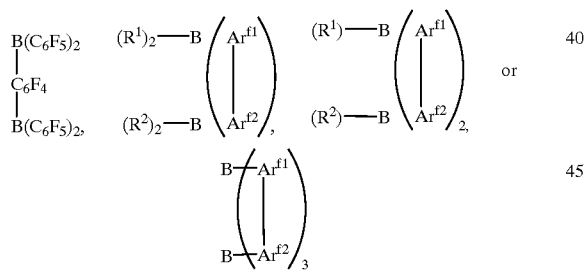

wherein:
$R^1$ and $R^2$ independently each occurrence are $C_{1-20}$ hydrocarbyl, halohydrocarbyl, or halocarbyl groups, and $Ar^{f1}$–$Ar^{f2}$ in combination, independently each occurrence, is a divalent fluoro-substituted aromatic group of from 6 to 20 carbons.

15. A catalyst system for polymerization of α-olefins comprising, the combination or reaction product of a Group 4 metal complex corresponding to the formula:

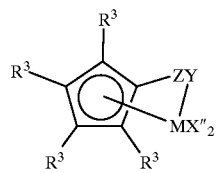

wherein:
M is titanium in the +2 formal oxidation state;
$R^3$ in each occurrence independently is selected from the group consisting of hydrogen, hydrocarbyl, silyl, germyl, cyano, halo and combinations thereof, said $R^3$ having up to 20 non-hydrogen atoms, or adjacent $R^3$ groups together form a divalent derivative thereby forming a fused ring system, two X" groups together form a neutral $C_{5-30}$ conjugated diene;

Y is —O—, —S—, —NR*—, —PR*—; and

Z is $SiR^*_2$, $CR^*_2$, $SiR^*_2SiR^*_2$, $CR^*_2CR^*_2$, $CR^*=CR^*$, $CR^*_2SiR^*_2$, or $GeR^*_2$, wherein $R^*$ is hydrogen or a group selected from silyl, hydrocarbyl, hydrocarbyloxy and combinations thereof, said $R^*$ having up to 30 carbon or silicon atoms, and a compound corresponding to the formula:

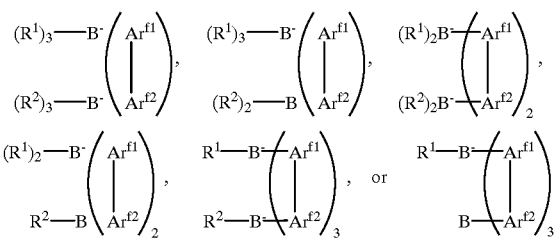

wherein:
$R_1$ and $R^2$ independently each occurrence are $C_{1-20}$ hydrocarbyl, halohydrocarbyl, or halocarbyl groups, and when connected to a negatively charged boron atom, one $R_1$ additionally comprises a cation selected from the group consisting of protonated cations of Bronsted acids, ferrocenium cations, carbonium cations, silylium cations, $Ag^+$, and cationic derivatives of a Group 3–10 metal complex and when connected to a negatively charged boron atom, one $R^2$ additionally comprises a cation selected from the group consisting of protonated cations of Bronsted acids, ferrocenium, carbonium cations, silylium cations, $Ag^+$, and cationic derivatives of a Group 3–10 metal complex; and an $Ar^{f1}$ group and an $Ar^{f2}$ group together form a $C_{6-20}$ divalent bridging group.

* * * * *